(12) United States Patent
Willis et al.

(10) Patent No.: US 10,045,837 B2
(45) Date of Patent: Aug. 14, 2018

(54) POROUS METAL DENTAL IMPLANT

(71) Applicant: Zimmer, Inc., Warsaw, IN (US)

(72) Inventors: Edward M. Willis, Hoboken, NJ (US);
Scott V. Cron, Wayne, NJ (US); Ryan Hollenbeck, Tigard, OR (US)

(73) Assignee: Zimmer, Inc., Warsaw, IN (US)

( * ) Notice: Subject to any disclaimer, the term of this patent is extended or adjusted under 35 U.S.C. 154(b) by 0 days.

(21) Appl. No.: 14/604,052

(22) Filed: Jan. 23, 2015

(65) Prior Publication Data

US 2015/0132719 A1    May 14, 2015

Related U.S. Application Data

(63) Continuation of application No. 13/947,440, filed on Jul. 22, 2013, now Pat. No. 8,939,764.

(60) Provisional application No. 61/674,610, filed on Jul. 23, 2012.

(51) Int. Cl.
*A61C 8/00* (2006.01)
*A61K 6/04* (2006.01)

(52) U.S. Cl.
CPC .......... *A61C 8/0009* (2013.01); *A61C 8/0012* (2013.01); *A61C 8/0022* (2013.01); *A61K 6/04* (2013.01)

(58) Field of Classification Search
CPC ....... A61C 8/00; A61C 8/0004; A61C 8/0006; A61C 8/0007; A61C 8/0009; A61C 8/001; A61C 8/0012–8/0048; A61C 8/0083; A61C 8/0086; A61C 8/0093–8/0098; A61C 2008/0084

USPC ........................................... 623/17.17–17.19
See application file for complete search history.

(56) References Cited

U.S. PATENT DOCUMENTS

| | | |
|---|---|---|
| 4,522,596 A | 6/1985 | Ashkinazy |
| 4,682,951 A | 7/1987 | Linkow |
| 5,004,421 A * | 4/1991 | Lazarof ............... A61C 8/0033 433/173 |
| 5,282,861 A | 2/1994 | Kaplan |

(Continued)

FOREIGN PATENT DOCUMENTS

| | | |
|---|---|---|
| EP | 0560279 A1 | 9/1993 |
| JP | 2004290418 A | 10/2004 |

(Continued)

OTHER PUBLICATIONS

"U.S. Appl. No. 13/947,440, Examiner Interview Summary dated Feb. 7, 2014", 4 pgs.

(Continued)

*Primary Examiner* — Edward Moran
(74) *Attorney, Agent, or Firm* — Schwegman Lundberg & Woessner, P.A.

(57) ABSTRACT

A dental augment system includes a porous metal augment, a solid metal insert, and a dental implant. The porous metal augment is sized for use in mandibular or maxillar bone. The porous metal material of the augment facilitates and promotes ingrowth of the surrounding bone into the porous metal structure, thereby rebuilding a suitable foundation for affixation of dental implants. The solid metal insert can be configured to be received within an insert bore of the porous metal augment and a dental implant can be received within and theradably engaged with a threaded bore of the solid metal insert.

9 Claims, 5 Drawing Sheets

(56) References Cited

U.S. PATENT DOCUMENTS

| | | | |
|---|---|---|---|
| 5,439,381 A * | 8/1995 | Cohen | A61C 8/001 433/173 |
| 6,309,220 B1 * | 10/2001 | Gittleman | A61B 17/176 433/173 |
| 6,450,812 B1 | 9/2002 | Laster et al. | |
| 7,682,152 B2 * | 3/2010 | Ford | A61C 8/0086 433/169 |
| 8,939,764 B2 | 1/2015 | Willis et al. | |
| 9,283,057 B2 * | 3/2016 | Sanders | A61C 1/084 |
| 2010/0003638 A1 * | 1/2010 | Collins | A61C 8/0012 433/174 |
| 2010/0114314 A1 | 5/2010 | Lomicka et al. | |
| 2011/0218628 A1 | 9/2011 | Ciupik et al. | |
| 2014/0023992 A1 | 1/2014 | Willis et al. | |

FOREIGN PATENT DOCUMENTS

| | | |
|---|---|---|
| WO | WO-2009004070 A1 | 1/2009 |
| WO | WO-2014018441 A2 | 1/2014 |
| WO | WO-2014018441 A3 | 1/2014 |

OTHER PUBLICATIONS

"U.S. Appl. No. 13/947,440, Non Final Office Action dated Jan. 8, 2014", 10 pgs.

"U.S. Appl. No. 13/947,440, Notice of Allowability dated Dec. 5, 2014", 7 pgs.

"U.S. Appl. No. 13/947,440, Notice of Allowance dated Sep. 12, 2014", 12 pgs.

"U.S. Appl. No. 13/947,440, Response filed Jul. 8, 2014 to Non-Final Office Action dated Jan. 8, 2014", 17 pgs.

"U.S. Appl. No. 13/947,440, Response filed Nov. 27, 2013 to Restriction Requirement dated Nov. 1, 2013", 7 pgs.

"U.S. Appl. No. 13/947,440, Restriction Requirement dated Nov. 1, 2013", 6 pgs.

"International Application Serial No. PCT/US2013/051466, International Search Report dated Feb. 10, 2014", 7 pgs.

"International Application Serial No. PCT/US2013/051466, Invitation to Pay Additional Fees and Partial Search Report dated Oct. 15, 2013", 4 pgs.

"International Application Serial No. PCT/US2013/051466, Written Opinion dated Feb. 10, 2014", 9 pgs.

"International Application Serial No. PCT/US2013/051466, International Preliminary Report on Patentability dated Feb. 5, 2015", 11 pgs.

"Australian Application Serial No. 2013293221, First Examiner Report dated Nov. 11, 2016", 3 pgs.

"Australian Application Serial No. 2013293221, Response filed Jan. 3, 2017 to First Examiner Report dated Nov. 11, 2016", 16 pgs.

"Australian Application Serial No. 2013293221, Response filed Jul. 27, 2017 Subsequent Examiners Report dated Feb. 13, 2017", 9 pgs.

"Australian Application Serial No. 2013293221, Subsequent Examiners Report dated Feb. 13, 2017", 3 pgs.

"European Application Serial No. 13745516.8, Communication Pursuant to Article 94(3) EPC dated Dec. 1, 2016", 4 pgs.

"European Application Serial No. 13745516.8, Response filed Apr. 11, 2017 to Communication Pursuant to Article 94(3) EPC dated Dec. 1, 2016", 53 pgs.

* cited by examiner

POROUS METAL DENTAL IMPLANT

CROSS-REFERENCE TO RELATED APPLICATION

This application is a continuation of U.S. patent application Ser. No. 13/947,440, filed on Jul. 22, 2013 which claims priority from U.S. Provisional Patent Application Ser. No. 61/674,610, filed on Jul. 23, 2012, the benefit of priority of each of which is claimed hereby, and each of which are incorporated by reference herein in its entirety.

TECHNICAL FIELD

The present disclosure relates to a dental prosthesis, and more particularly, to porous metal support structures suitable for use with dental implants.

BACKGROUND

Dental implants are commonly used as anchoring members in prosthodontics restorations to provide prosthetic teeth at one or more edentulous sites in a patient's dentition at which the patient's original natural teeth have been lost or damaged. Implant systems can include a dental implant made from a suitable biocompatible material, such as titanium. The dental implant can be threaded into a bore, which is drilled into the patient's mandible or maxilla at the edentulous site. The dental implant provides an anchoring member for a dental abutment, which is typically also made from a biocompatible metal such as titanium or ceramic. The dental abutment in turn provides an interface between the implant and a dental restoration. The dental restoration is typically a porcelain crown fashioned to replicate the shape of the tooth being replaced.

Many dental implant surgeries are performed in two stages. In the initial or first stage, an incision is made in the patient's gingiva at an edentulous site, and a bore is drilled into the patient's mandible or maxilla at the edentulous site, followed by threading or impacting a dental implant into the bore using a suitable driver. Thereafter, a cap is fitted onto the implant to close the abutment coupling structure of the implant, and the gingiva is sutured over the implant. Over a period of several months, the patient's jaw bone grows around the implant to securely anchor the implant in the surrounding bone, a process known as osseointegration.

In a second stage of the procedure following osseointegration, the dentist reopens the gingiva at the implant site and secures an abutment and optionally, a temporary prosthesis or temporary healing member, to the implant. Then, a suitable permanent prosthesis or crown is fashioned, such as from one or more impressions taken of the abutment and the surrounding gingival tissue and dentition. In this final stage, the temporary prosthesis or healing member is removed and replaced with the permanent prosthesis, which is attached to the abutment with cement or with a fastener, for example. Alternative single stage implants with integral emergence profiles or one-piece implants with integral abutments can be used, and can extend through the transgingival layer so that the gingiva need not be reopened to access the implant. If the patient has more than one tooth missing, multiple implants can be used to provide anchorage for a denture bar, a bridge, or other prosthodontic appliance.

To drill holes in the jawbone of a patient, an oral surgeon can use a drill guide, which is typically formed as a custom patient-specific appliance that overlays the drill site and at least a portion of the surrounding gum tissue and/or dentition. The drill guide includes a hole aligned along the intended drill axis, and one or more removable drill guide tubes can be positioned within the drill guide hole to allow drills of different diameters to be used in succession for drilling the holes in the jawbone in which the dental implants will be secured.

SUMMARY

The present inventors have recognized, among other things, that when a large section of the mandibular or maxillar bone has been compromised or destroyed, such as by disease or trauma, insufficient bone stock can be present for threadably affixing a dental implant to bone at the edentulous site. In such instances, the edentulous site can provide an unsuitable foundation (e.g., insufficient bone stock) for affixation of the dental implant. The unsuitable foundation can preclude the use of conventional dental implants that are used as an anchoring member.

The present disclosure provides a porous metal augment for use in mandibular or maxillar bone. The porous metal material of the porous metal augment can facilitate and promote ingrowth of the surrounding bone into the porous metal structure, thereby rebuilding a suitable foundation for affixation of dental implants. A core can be embedded within the porous metal body of the porous metal augment, and is made of a material suitable for firm threaded fixation of dental implants thereto. For example, the metal core can be formed of a titanium structure, which has sufficient strength and resiliency to form a firm and long lasting threaded connection with a threaded stem of a dental implant.

To better illustrate the porous metal dental implant, a non-limiting list of examples is provided here:

In Example 1, a dental augment comprises a porous metal augment sized and shaped for implantation into at least one of a mandible and a maxilla, the porous metal augment having an insert bore formed therein, and a solid metal insert having a threaded bore sized to threadably attach to a dental implant, the solid metal insert received within the insert bore formed in the porous metal augment.

In Example 2, the dental augment of Example 1 is optionally configured such that the solid metal insert is formed from at least one of titanium and cobalt-chrome-molybdenum.

In Example 3, the dental augment of any one or any combination of Examples 1 and 2 is optionally configured in combination with a dental implant, such that the dental implant includes a threaded implant portion sized to be threadably coupled with the threaded bore of the solid metal insert.

In Example 4, the dental augment of any one or any combination of Examples 1 through 3 is optionally configured such that the porous metal augment comprises a counterbore positioned at a first end of the insert bore.

In Example 5, the dental augment of any one or any combination of Examples 1 through 4 is optionally configured such that the solid metal insert comprises a shoulder sized to be received within the counterbore.

In Example 6, the dental augment of any one or any combination of Examples 1 through 5 is optionally configured such that a thickness of the shoulder is equal to a depth of the counterbore.

In Example 7, the dental augment of any one or any combination of Examples 1 through 6 is optionally configured such that a thickness of the shoulder is less than a depth of the counterbore.

In Example 8, the dental augment of any one or any combination of Examples 1 through 7 is optionally configured such that the insert bore comprises a circular cross-section perpendicular to a longitudinal axis of the insert bore and the counterbore comprises a noncircular cross-sectional perpendicular to the longitudinal axis In Example 9, the dental augment of any one or any combination of Examples 1 through 8 is optionally configured such that the solid metal insert comprises a receiving shaft defining the threaded bore, the receiving shaft configured to be received within the insert bore.

In Example 10, a dental augment comprises a porous metal augment sized to be received in a cavity formed in at least one of a mandible and a maxilla, the porous metal augment having a first bore defining a first bore axis and a second bore defining a second bore axis, a core receivable within the first bore along the first bore axis, and an adaptor insertable into the second bore formed along the second bore axis, the adaptor configured to be affixable to the core.

In Example 11, the dental augment of any one or any combination of Examples 1 through 10 is optionally configured such that the core and the adapter are formed from at least one of titanium and cobalt-chrome-molybdenum.

In Example 12, the dental augment of any one or any combination of Examples 1 through 11 is optionally configured in combination with a dental implant, such that the adaptor defines a first threaded bore configured to be threadably coupled with a threaded implant portion of the dental implant.

In Example 13, the dental augment of any one or any combination of Examples 1 through 12 is optionally configured such that the core includes a second threaded bore.

In Example 14, the dental augment of any one or any combination of Examples 1 through 13 is optionally configured such that an exterior surface of the adapter is threaded and configured to be threadably engaged with the second threaded bore of the core.

In Example 15, the dental augment of any one or any combination of Examples 1 through 14 is optionally configured such that the second bore extends from a superior surface of the porous metal augment into the first bore.

In Example 16, the dental augment of any one or any combination of Examples 1 through 15 is optionally configured such that the first bore is in communication with the second bore.

In Example 17, the dental augment of any one or any combination of Examples 1 through 16 is optionally configured such that the second bore axis is substantially perpendicular to the first bore axis.

In Example 18, the dental augment of any one or any combination of Examples 1 through 17 is optionally configured such that the second bore axis is oblique to the first bore axis.

In Example 19, a dental augment system comprises a porous metal augment sized and shaped for implantation into a mandible or maxilla, the porous metal augment having an insert bore formed therein, a solid metal insert having a threaded bore configured to be positioned within the insert bore, and a dental implant having a threaded implant portion configured to be threadably coupled with the threaded bore of the solid metal insert.

In Example 20, the dental augment of any one or any combination of Examples 1 through 19 is optionally configured such that the solid metal insert is formed from at least one of titanium and cobalt-chrome-molybdenum.

In Example 21, a method of forming a dental augment includes forming a porous metal augment having an insert bore extending from a first surface to a second surface, the first surface opposite the second surface, forming a solid metal insert having a threaded bore, the solid metal insert configured to be inserted into the insert bore, and coupling the solid metal insert within the insert bore.

In Example 22, the method of any one or any combination of Examples 1 through 21 is optionally configured to include forming a counterbore at a first end of the insert bore.

In Example 23, the method of any one or any combination of Examples 1 through 22 is optionally configured such that forming the solid metal insert comprises forming a solid metal insert having a shaft and a shoulder.

In Example 24, the method of any one or any combination of Examples 1 through 23 is optionally configured such that coupling the solid metal insert to the porous metal augment comprises inserting the shaft into the insert bore such that the shoulder is received within the counterbore.

In Example 25, a method of forming a dental augment includes forming a porous metal augment having a first bore defining a first bore axis and a second bore defining a second bore axis, coupling a core within the first bore along the first bore axis, the core having a first threaded bore, inserting an adaptor within the second bore formed along the second bore axis, and coupling the adaptor to the core within the porous metal augment.

In Example 26, the method of any one or any combination of Examples 1 through 25 is optionally configured such that forming the adaptor comprises forming threads on an exterior surface of the adaptor.

In Example 27, the method of any one or any combination of Examples 1 through 26 is optionally configured such that coupling the adaptor to the core within the porous metal augment includes engaging the threads on the exterior surface of the adaptor with the first threaded bore.

In Example 28, a method includes inserting a dental augment, including an insert bore formed therein, and a solid metal insert having a threaded bore, the solid metal insert received within the insert bore formed in the porous metal augment, into a dental bone cavity, and coupling a dental implant, including a threaded portion, to the dental augment.

In Example 29, the method of any one or any combination of Examples 1 through 28 is optionally configured such that coupling the dental implant to the dental augment includes threadably engaging the threaded portion into the threaded bore.

In Example 30, a method includes inserting a dental augment, including a porous metal augment having a first bore defining a first bore axis and a second bore defining a second bore axis, a core receivable within the first bore along the first bore axis, and an adaptor insertable into the second bore formed along the second bore axis, the adaptor configured to be affixable to the core, into a dental bone cavity, and coupling a dental implant, including a threaded portion, to the dental augment.

In Example 31, the method of any one or any combination of Examples 1 through 30 is optionally configured such that coupling the dental implant to the dental augment includes threadably engaging the threaded portion into the a threaded bore of the adaptor.

These and other examples, advantages, and features of the present porous metal dental implants will be set forth in part in the following Detailed Description and the accompanying drawings. This Overview is intended to provide non-limiting examples of the present subject matter—it is not intended to provide an exclusive or exhaustive explanation. The Detailed Description and drawings are included to provide further information about the present porous metal dental implants.

BRIEF DESCRIPTION OF THE DRAWINGS

The above-mentioned and other features and advantages of this disclosure, and the manner of attaining them, will become more apparent and will be better understood by reference to the following description of embodiments of the disclosure taken in conjunction with the accompanying drawings.

Corresponding reference characters indicate corresponding parts throughout the several views. The exemplifications set out herein illustrate exemplary embodiments of the present invention, and such exemplifications are not to be construed as limiting the scope of the invention in any manner.

DETAILED DESCRIPTION

The present disclosure provides a dental augment that can be suitable for implantation, such as into a prepared cavity in mandibular or maxillar bone beyond the gum line, such that adjacent mandibular or maxillar bone can grow into the porous metal material of the augment to provide a stable foundation of support such as for dental implants. In order to ensure secure long-term coupling of the dental implants to the porous metal augment, the porous metal augment can include an insert or core made of a material suitable for threaded fixation, such as titanium, to fixedly engage with a dental implant.

A porous metal augment in accordance with the present disclosure can be formed from a porous material such as a single piece of highly porous biomaterial. A highly porous biomaterial is useful as a bone substitute and as cell and tissue receptive material. A highly porous biomaterial can have a porosity as low as 55%, 65%, or 75% or as high as 80%, 85%, or 90%, or can have any porosity within any range defined by any of the foregoing values. An example of such a material can be produced using Trabecular Metal™ Technology generally available from Zimmer, Inc., of Warsaw, Ind. Trabecular Metal™ is a trademark of Zimmer, Inc. Such a material can be formed from a reticulated vitreous carbon foam substrate which can be infiltrated and coated with a biocompatible metal, such as tantalum, etc., by a chemical vapor deposition ("CVD") process such as in the manner disclosed in detail in U.S. Pat. No. 5,282,861 to Kaplan, the entire disclosure of which is expressly incorporated herein by reference. In addition or alternative to tantalum, one or more other metals such as niobium, or one or more alloys of tantalum and niobium with one another or with one or more other metals can be used.

Figure 5:
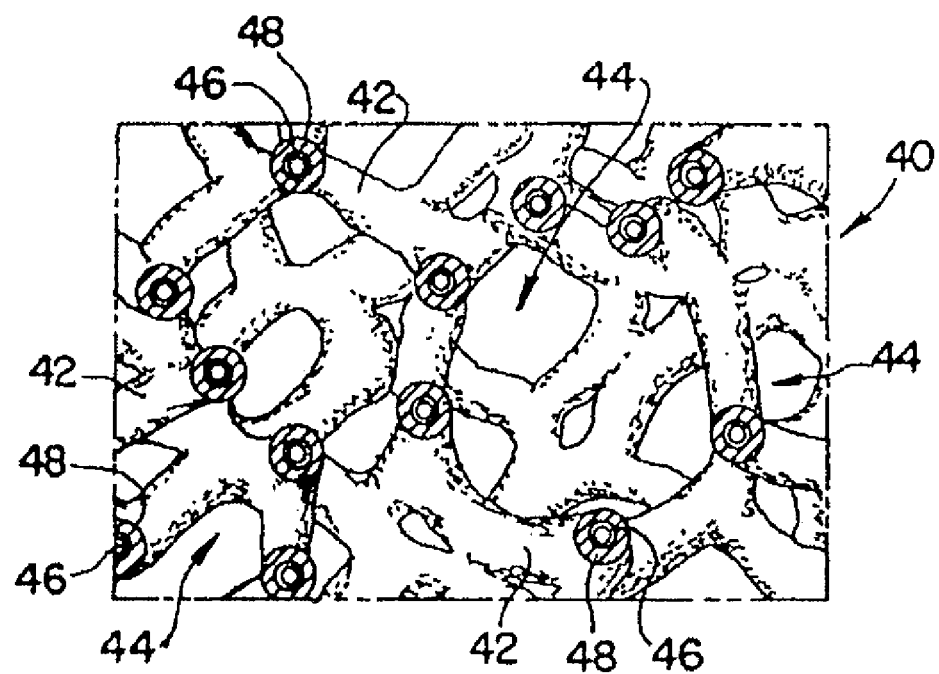
FIG. 5 is an enlarged fragmentary view of the portion of the porous tantalum forming the dental augments of FIGS. 1-4 in accordance with at least one example of the present invention.

Generally, as shown in FIG. 5, the porous tantalum structure 40 can include a large plurality of ligaments 42 defining open spaces 44 therebetween, with each ligament 42 generally including a carbon core 46 covered by a thin film of metal 48 such as tantalum, for example. The open spaces 44 between the ligaments 42 can form a matrix of continuous channels having no dead ends, such that growth of cancellous bone through the porous tantalum structure 40 is uninhibited. The porous tantalum or other metal 48 can include up to 75%, 85%, or more void space therein. Thus, porous tantalum or other metal 48 can provide a lightweight, strong porous structure that is substantially uniform and consistent in composition, and can closely resemble the structure of natural cancellous bone, thereby providing a matrix into which cancellous bone can grow to provide fixation of the support structure to the patient's bone.

The porous tantalum structure 40 can be made in a variety of densities such as to selectively tailor the structure for particular applications. In particular, as discussed in the above-incorporated U.S. Pat. No. 5,282,861, the porous tantalum can be fabricated to virtually any desired porosity and pore size, and can thus be matched with the surrounding natural bone in order to provide an improved matrix for bone ingrowth and mineralization.

Figure 1:
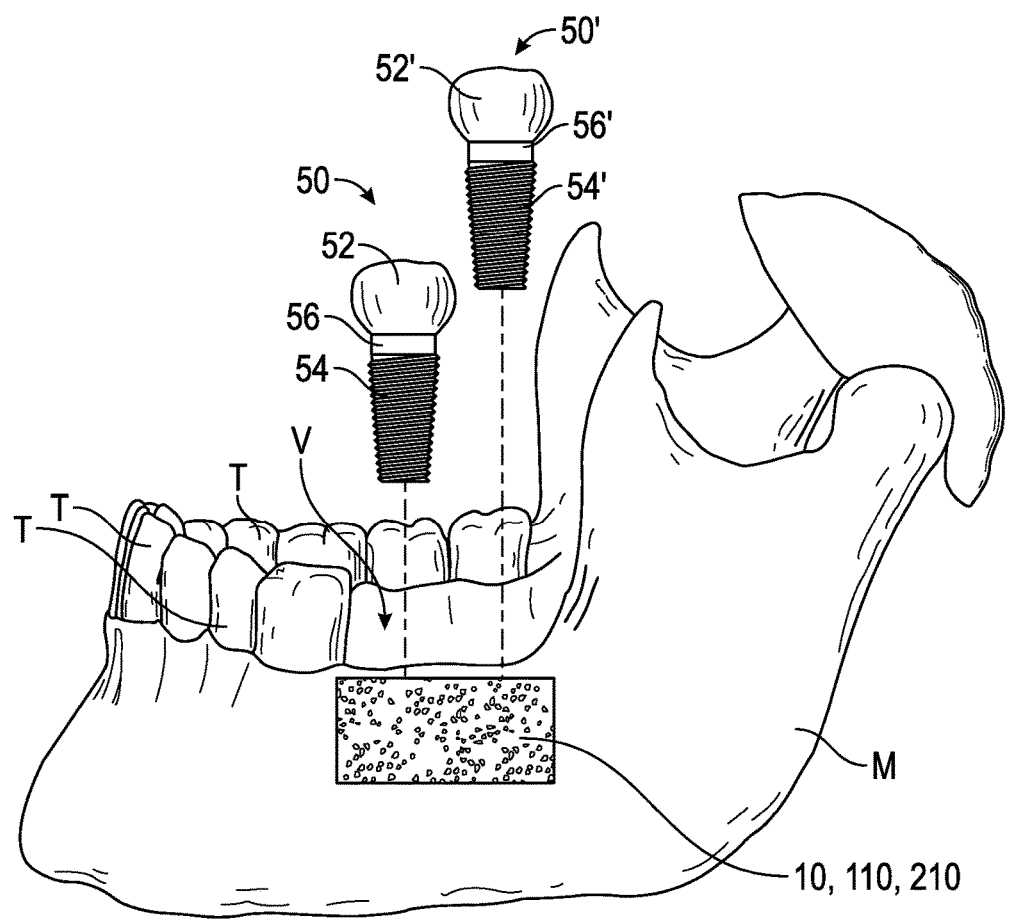
FIG. 1 is a side elevation view of a dental augment in accordance with at least one example of the present disclosure, shown in an implanted location within a human mandible and in conjunction with a pair of dental implants.

Turning now to FIG. 1, a side elevation view of a dental augment 10, 110, 210 in accordance with at least one example of the present disclosure, shown in an implanted location within a human mandible "M" and in conjunction with a pair of dental implants 50, 50'. The augments 10, 110, 210 (described in detail below) are shown embedded within the bony mass of human mandible "M" below the gum line. As illustrated, mandible "M" has a plurality of healthy teeth "T" but has void "V" in the vicinity of the left molars. Void "V" can have resulted from trauma, disease, or deterioration of the healthy natural teeth, for example.

In some cases, void "V" can be cured by implanting implants 50, 50' directly into the bone stock of mandible "M", as discussed herein. Implants 50, 50' can be formed as an assembly including a tapered, threaded implanted portion 54, 54' (referred to interchangeably as "threaded portions 54, 54'), a crown or prosthesis 52, 52' and an abutment 56, 56' connecting crown 52, 52' to threaded portions 54, 54' respectively. As discussed herein, an appropriately sized bore is normally first prepared in the surrounding healthy bone stock. The prepared bore is sized to engage the threaded portions 54, 54' of dental implants 50, 50'. However, in some cases, the bone stock normally used to engage the threaded portions 54, 54' is damaged, diseased or otherwise impaired and therefore unsuitable for direct coupling of the threaded portions 54, 54'. In such cases, the impaired bone stock can be removed by traditional surgical methods, such as reaming, milling, drilling, and/or other traditional techniques suitable for creating cavities of a desired shape and geometry within the mandibular bone.

As illustrated in the example of FIG. 1, after creating an appropriately sized cavity sized and shaped to fit one of the augments 10, 110, 210 such augment can be implanted into the prepared cavity. In some instances, bone cement can be used for initial fixation of the augments 10, 110, 210 to the surrounding bone of mandible "M". It is appreciated that the porous metal material of the augment 10, 110, 210 is designed to promote bone ingrowth and therefore can cause the adjacent mandibular bone to form a permanent fixation of the augments 10, 110, 210 in its implanted location with or without bone cement.

Once one of the augments 10, 110, 210 are firmly affixed to the bone of mandible "M", the dental implants 50, 50' can be engaged with the augments 10, 110, and 210 to firmly affix the dental implants 50, 50' therewith, as described herein.

The dental implants 50, 50' include first and second prosthetic molar crowns 52, 52', respectively. Molar crowns 52, 52', as illustrated in the example of FIG. 1, can be appropriate for use in void "V" because the natural first and second molars are missing from mandible "M". However, the augments 10,110, 210 can be used for any of the teeth in mandible "M", or for any teeth in the maxilla (not shown), by appropriately sizing and configuring the augments 10, 110, 210 to fit within a cavity in the appropriate adjacent bone stock. Moreover, although the augments 10, 110, 210 each illustrate a size and configuration appropriate for implantation of a neighboring pair of prosthetic teeth (i.e., dental implants 50 and 50'), it is contemplated that the augments 10, 110, 210, in accordance with the present disclosure, can be shaped and sized to replace any number of teeth in any mammalian mandible or maxilla. For example, the augments 10, 110, 210 can be formed as an arcuate augment designed to extend around part or the entire arcuate path normally defined by the natural teeth. In one embodiment, the augments 10, 110, 210 can be sized to extend around half of mandible "M" (or the maxilla) and therefore can be adapted to provide a base of support for prosthetic teeth on the entire left or right half of the patient's dentition.

Figure 2:
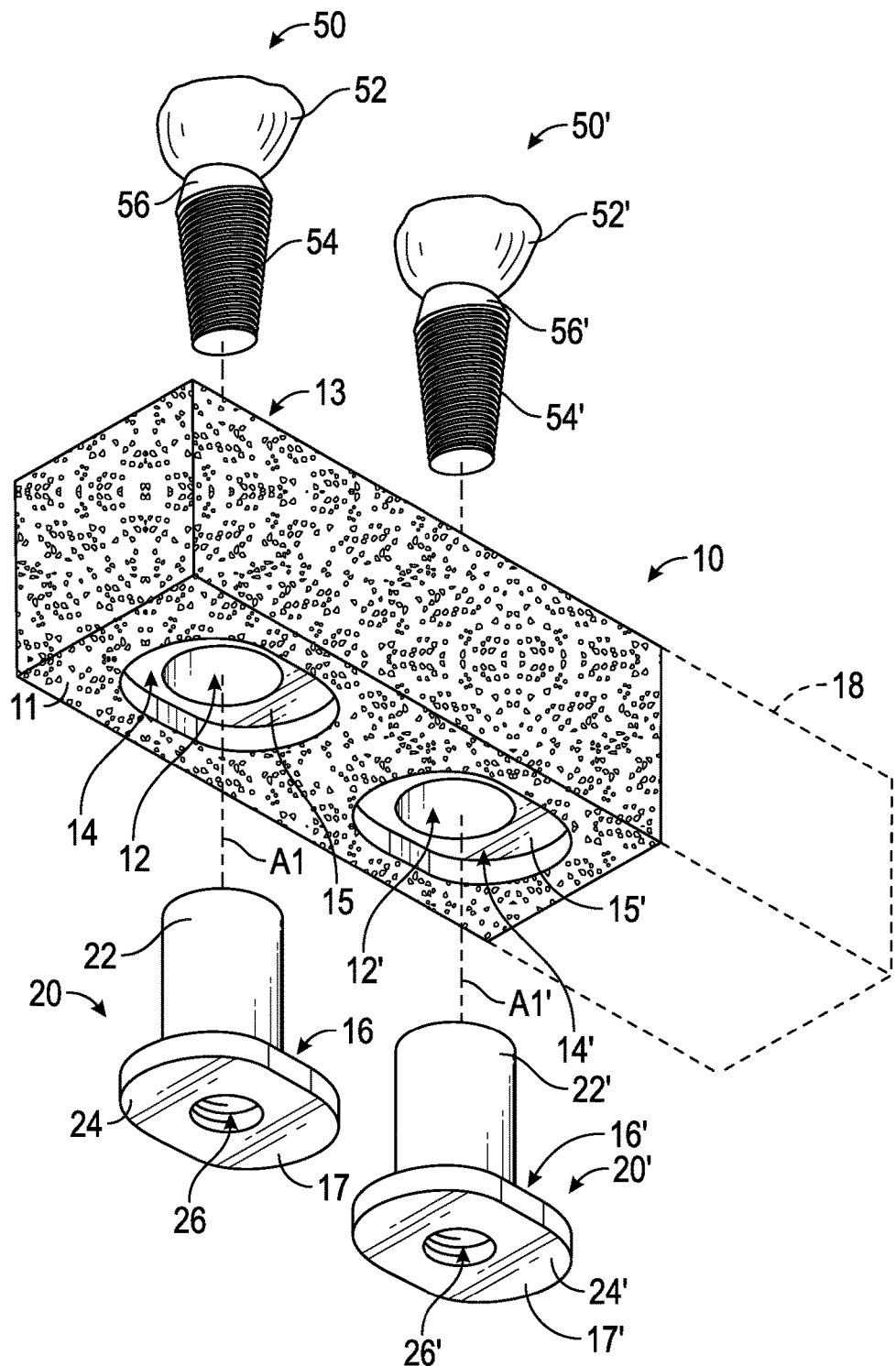
FIG. 2 is a perspective, exploded view of a dental augment in accordance with at least one example of the present disclosure.

Turning now to FIG. 2, a perspective, exploded view of a dental augment 10 (herein referred to interchangeable as "augment 10") in accordance with at least one example of the present disclosure is shown. The augment 10 is shown in conjunction with dental implants 50, 50'. The augment 10 has a substantially square shaped cross-sectional profile and an elongated longitudinal extent. The augment 10 can include an inferior surface 11 and a superior surface 13.

In an example, the augment 10 can have any cross-sectional profile shape. In the example shown in FIG. 1, the augment 10 can include a square cross-section profile shape. In another example, the augment 10 can have a cross-section profile shape including, but not limited to, a circle, oval, ellipse, and semi-circle, among others. The augment 10 can have an elongate and/or arcuate longitudinal extent suitable for implantation within various parts of mandible "M" or a maxilla. For example, the augment 10 can include extension 18 that is monolithically formed therewith or mechanically attached thereto. The extension 18 can be sized to expand the overall longitudinal extent of the augment 10. Expanding the overall longitudinal extent of the augment 10 can facilitate the use of additional dental implants. The example shown in FIG. 1 illustrates the use of two dental implants 50, 50'. However, the extension 18 can facilitate the use of more than two dental implants such as three, four, and five.

The augment 10 can include bores 12, 12' extending through the body of augment 10. The augment 10 can include counterbores 14, 14' formed at a first end of the bores 12, 12'. The bores 12, 12' can extend from counterbore surfaces 15, 15' to the superior surface 13. The counter bores 14, 14' can extend from the inferior surface 11 to the counter bore surfaces 15, 15'.

In the example illustrated in FIG. 1, the bores 12 and 12' have the same size and geometry adapted to receive shafts 22, 22' of inserts 20, 20', as described herein. However, the bores 12, 12', the counterbores 14, 14', and the associated features of the inserts 20, 20' can vary with respect to one another, such as to accommodate differently sized dental implants 50, 50'. In the example illustrated in FIG. 1, however, the threaded portions 54, 54' of dental implants 50, 50' are the same and therefore the associated structures used for coupling the threaded portions 54, 54' to augment 10 can also be the same.

For clarity, the coupling of the insert 20 to the augment 10 and of the dental implant 50 to the insert 20 will be described. However, the insert 20' and the implant 50' can be coupled to the augment 10 in a similar fashion.

The insert 20 is sized to be received within the augment 10 as described herein, and is made from a material suitable for firm threaded engagement with the dental implant 50. In an example, one or more materials for insert 20 can include, but are not limited to, titanium and alloys thereof, Cobalt-Chrome-Molybdenum (CoCrMo) and alloys thereof. Other biocompatible materials with sufficient density and resiliency for stable threaded fixation can also be used.

The insert 20 can include a shaft 22 and a shoulder 24. The shaft 22 can be sized to be received within the bore 12 formed through the augment 10. The shoulder 24 can be sized to be received within the counterbore 14 formed at a first end of the bore 12. In an example, the bore 12 and the shaft 22 are sized to form a press fit therebetween, such that shaft 22 is securely received within bore 12 so as to be immovable along directions oblique to axis A1 when insert 20 is coupled to the dental augment 10. Similarly, the shoulder 24 can form a press fit with the counterbore 14 to also be snugly received therewithin.

As illustrated, the shoulder 24 defines a noncircular cross-section along its axial extent, which cooperates with a correspondingly noncircular cross-section of counterbore 14. The noncircular cross-section of the shoulder 24 and of the counterbore 14 can prevent or limit rotation of the insert 20 about a longitudinal axis A1 of bore 12 and insert 20. In the example illustrated in FIG. 2, the shoulder 24 defines an oval cross-section, though other noncircular cross-sections can be employed that provide the similar effect of preventing or limiting rotation. Alternatively, the shoulder 24 can be pinned, adhered or otherwise affixed within the counterbore 14 to prevent rotation of the insert 20. In one example, at least one of the shoulder 24 and the shaft 22 can be bonded to the augment 10. For example, the at least one of the shoulder 24 can be bonded to the counterbore surface 15 and the shaft 22 can be bonded to the bore 12. The at least one of the shoulder 23 and the shaft 22 can be bonded to the augment 10 by using electric resistance welding, diffusion bonding, or another bonding technique. Electric resistance welding can include spot welding, seam welding flash welding, resistance projection welding, and upset welding.

In an example, the shoulder 24 has a thickness (e.g., a longitudinal extent along axis A1) that is less than or equal to the corresponding depth of counterbore 14. When the insert 20 is fully received within the bore 12 and the counterbore 14, a contact surface 16 contacts or is adjacent to the counterbore surface 15 and an exposed surface 17 of the shoulder 24 is either flush with, or recessed within, the adjacent surface (e.g., the inferior surface 11) of the augment 10. That is, the thickness of the shoulder 24 is equal to or less than a depth of the counterbore 14 (e.g., distance from counterbore surface 15 to inferior surface 11). This arrangement promotes firm and flush contact of the porous metal surface of the augment 10 with adjacent bone.

The insert 20 can include a threaded bore 26 formed therethrough along axis A1. The threaded bore 26 can be sized and arranged to mate with threaded portion 54 of dental implant 50 to form a firm threaded fixation therebetween. As illustrated in the example of FIG. 1, the threaded bore 26 can extend through the entire length of the insert 20. In an example, the threaded bore 26 does not extend through the shoulder 24 and terminates prior to the exposed surface 17.

When the dental implant 50 is affixed, the dental implant 50 and insert 20 can be drawn together, thereby urging shoulder 24 into firm contact with counterbore 14. The solid (e.g., non-porous) material of the insert 20 can facilitate a strong and stable axial fixation of dental implant 50 by facilitating a robust threaded connection, while the large surface area contact between the shoulder 24 and the counterbore 14 provides a counterbalancing force for this threaded connection and facilitates a firm coupling of implant 50 to augment 10 without damage or significant deformation of the relatively less dense porous metal material of implant 50.

Figure 3:
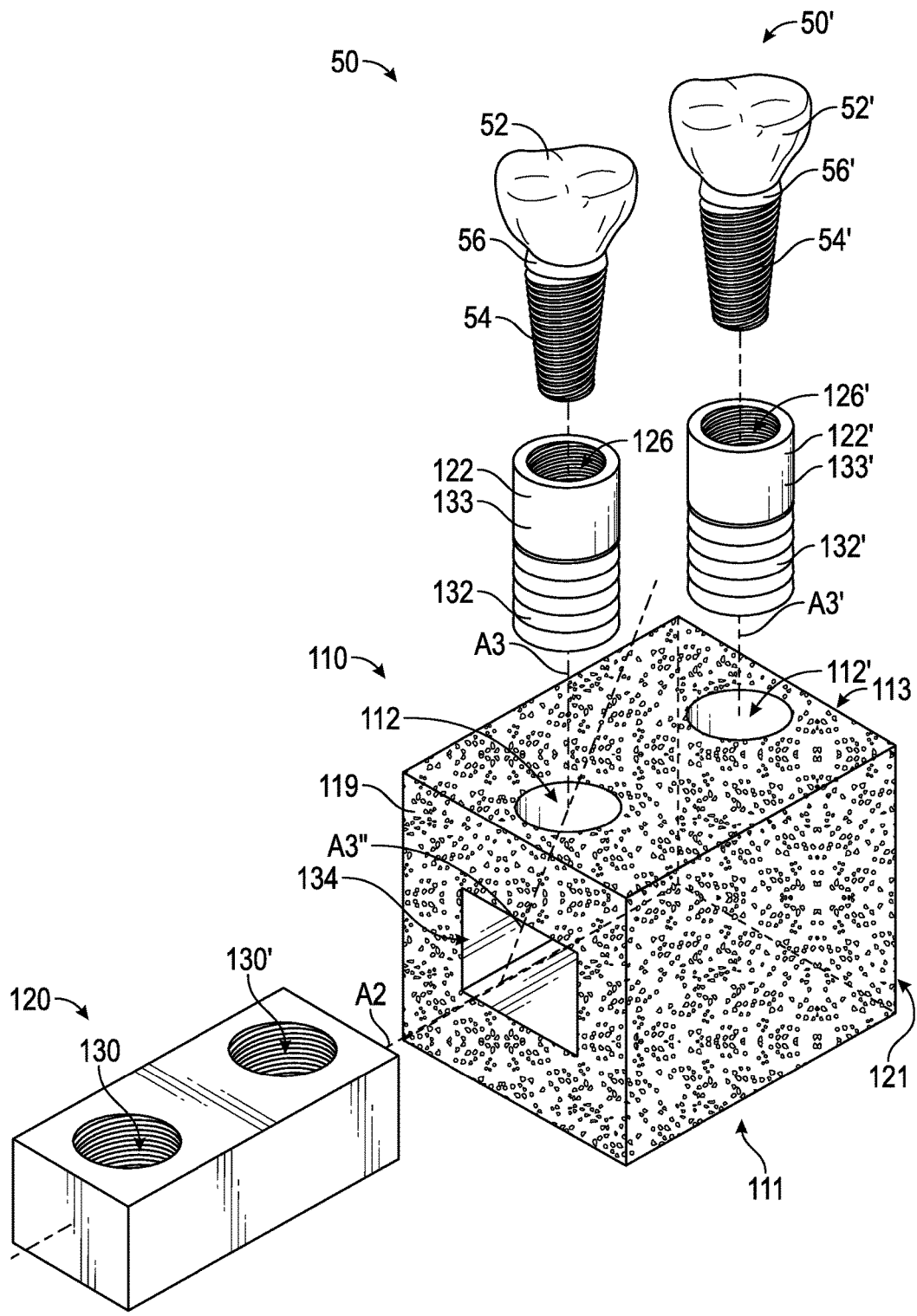
FIG. 3 is a perspective, exploded view of a dental augment in accordance with at least one example of the present disclosure.

Turning now to FIG. 3, a perspective, exploded view of a dental augment 110 (herein referred to interchangeable as "augment 110") in accordance with at least one example of the present disclosure is shown. The augment 110 is similar to augment 10 described herein, with reference numerals of augment 110 analogous to corresponding reference numerals used in augment 10, except with 100 added thereto. Structures of augment 110 correspond to similar structures denoted by corresponding reference numerals of augment 10 except as otherwise noted.

The augment 110 can include a longitudinal bore 134 along longitudinal axis A2. The longitudinal bore 134 can extend from a first side wall 19 to a second side wall 20 of the augment 11. In an example, the longitudinal bore 134 extends only partially into the augment 110. That is, the longitudinal bore 134 terminates prior to reaching the second side wall 20. The augment 110 can include bores 112, 112' extending through the body of augment 110. The bores 112, 112' can extend from the superior surface 113 to the longitudinal bore 134. That is, the bores 112, 112' are in communication with the longitudinal bore 134.

The augment 110 dispenses with inserts 20, 20' (as shown in FIG. 1), and instead utilizes a core 120 and/or adaptors 122, 122' to provide a stable foundation for attachment of dental implants 50, 50' to augment 110. Similar to the insert 20 in FIG. 1, core 120 can be formed from a solid (e.g., non-porous) material such as titanium, CoCrMo, or alloys thereof. The core 120 defines internally threaded bores 130, 130'. The core 120 can be receivable within the longitudinal bore 134 along the longitudinal axis A2. The core 120 and the longitudinal bore 134 are correspondingly shaped such that the longitudinal bore 134 can receive the core 120. As illustrated in the example of FIG. 3, the longitudinal bore 134 and the core 120 have a cross-sectional shape of a square. However, other shapes can be used.

The adaptors 122, 122' can be sized to be received within the bores 112, 112'. The adaptors 122, 122' can define threaded bores 126, 126' that are configured to receive the threaded portions 54, 54' of the dental implants 50, 50'. The adaptors 122, 122' can include threaded portions 132, 132' and non-threaded portions 133, 133'. In an example, the threaded portions 132, 132' can be configured to be theradably engaged with the internally threaded bores 130, 130' of the core 120. In an example, the non-threaded portions 133, 133' can be configured to be positioned within the bores 112, 112'. The core 120 can provide a firm and stable threaded engagement with the external threads 132, 132' of the adaptors 122, 122'.

In an example, the adaptors 122, 122' can be omitted and the threaded portions 54, 54' of the dental implants 50, 50' can thread directly into the threaded bores 130, 130' of the core 120. In another example, the core 120 can be omitted and only the adaptors 122, 122' are used as anchors for the threaded portions 54, 54' of the dental implants 50, 50'. That is the threaded portions 54, 54' of the dental implants 50, 50' can thread directly into the threaded bores 126, 126' of the adaptors 122, 122'.

As discussed herein, the core 120 can be received within the longitudinal bore 134 along the longitudinal axis A2 thereof. When the core 120 is fully received within the longitudinal bore 134, a longitudinal axis of bores 130, 130' formed in core 120 align along transverse axes A3, A3', respectively, In an example, the transverse axes A3, A3' can be oblique to the longitudinal axis A2 of the bore 134. As illustrated in the example of FIG. 3, the axis A2 is substantially perpendicular to the axes A3, A3'. Adaptors 122, 122' can be advanced toward core 120 along the axes A3, A3', respectively, and threadably affix to the core 120 by engaging the external threads 132, 132' with the internal threads formed within the bores 130, 130'.

After the core 120 is inserted into the augment 10 and the adaptors 122, 122' are coupled to the core 120, an augment preassembly including augment 110, core 120 and adaptors 122, 122' is complete. This preassembly can be implanted into a correspondingly formed cavity in mandible "M", as shown in FIG. 1, or in any other location in a mandible or maxilla where dental implants can be used. In the example illustrated in FIG. 3, the dental implants 50, 50' can be coupled to the augment preassembly by threadably engaging threaded portions 54, 54' with the corresponding internal threads of bores 126, 126' formed in adaptors 122, 122', respectively.

Figure 4:
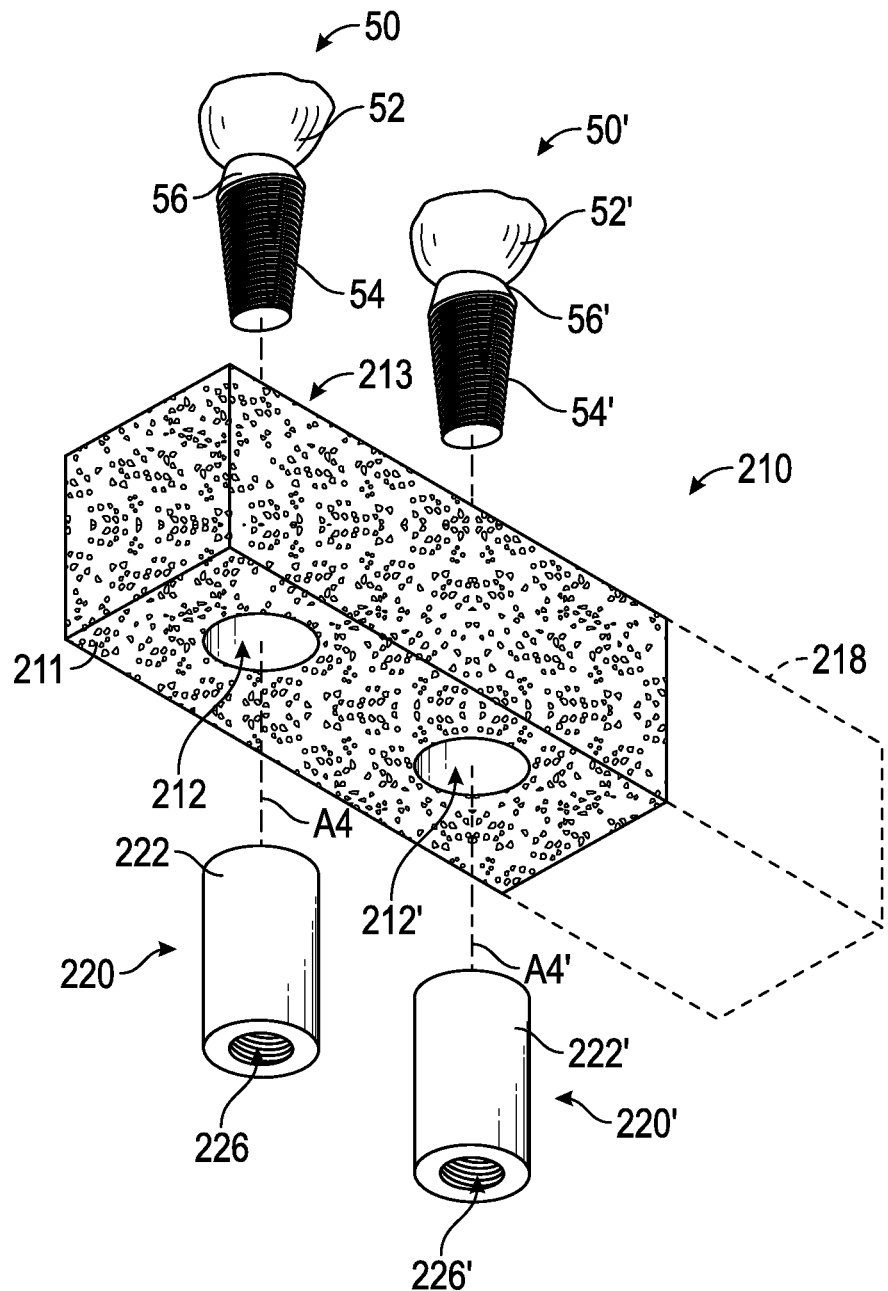
FIG. 4 is a perspective, exploded view of a dental augment in accordance with at least one example of the present disclosure.

Turning to FIG. 4, a perspective, exploded view of a dental augment 210 (referred to herein as "augment 210") in accordance with at least one example of the present disclosure is shown. The augment 210 is similar to augments 10, 110 described herein, with reference numerals of augment 210 analogous to corresponding reference numerals used in augments 10, 110, except with 200 added thereto. Structures of augment 210 correspond to similar structures denoted by corresponding reference numerals of augments 10, 110 except as otherwise noted. The augment 210 illustrated in FIG. 4 is similar to the augment 10 in FIG. 1, however, the inserts 222, 222' in FIG. 4, do not include the shoulder (e.g., shoulder 24 in FIG. 2) and the dental augment 10 does not include the counterbores (e.g., counterbores 14, 14' in FIG. 2).

The augment 210 is shown in conjunction with dental implants 50, 50'. The augment 210 has a substantially square shaped cross-sectional profile and an elongated longitudinal extent. The augment 210 can include an inferior surface 211 and a superior surface 213. As discussed herein, the augment 210 can have any elongate and/or arcuate longitudinal extent suitable for implantation within various parts of mandible "M" or a maxilla. For example, augment 210 can include extension 218 monolithically formed therewith or mechanically attached thereto. The extension 218 can be sized to expand the overall longitudinal extent of the augment 210.

The augment 210 can include bores 212, 212' extending through the body of augment 210. The bores 212, 212' can extend from an inferior surface 211 to a superior surface 213. In the example illustrated in FIG. 4, bores 212 and 212' have the same size and geometry adapted to receive shafts 222, 222' of inserts 220, 220', as described herein. The bores 212, 212' and the shafts 222, 222' can be sized to form a press fit therebetween, such that shaft 22 is securely received within bore 12 so as to be immovable along directions oblique to axis A4 when insert 220 is coupled to dental augment 210.

In an example, the cross-section of the bores 212, 212' and the external surface of the shafts 222, 222' can have a non-circular cross-section to prevent or limit rotation of the inserts 220, 220' about a longitudinal axes A4, A4 when the threaded portions 54, 54' are being threadably engaged with the threaded bores 226, 226' of the inserts 222, 222'. The threaded bores 226, 226' and the threaded portions 54, 54' can have a substantially circular cross-section to facilitate threading the threaded portions 54, 54' into the threaded bores 226, 226'.

In an example, the shafts 222, 222' of the inserts 220, 220' can be bonded to the dental augment 210. For example, the shafts 222, 222' can be bonded to the bores 212, 212' of the dental augment 210 by using electric resistance welding, diffusion bonding, or another bonding technique. Electric resistance welding can include spot welding, seam welding flash welding, resistance projection welding, and upset welding.

Advantageously, augments 10, 110, 210 can be implanted into a region of damaged or diseased bone of a mandible or maxilla at the time of dental surgery, while reserving use of dental implants until a later time. When it is determined that augments 10 or 110 has achieved stable fixation with the surrounding bone such that a surgeon or other dental professional deems it appropriate to utilize dental implants, the threaded bores presented by inserts 20, 20' or adaptors 122, 122' can be exposed and appropriate dental implants can be coupled thereto.

Moreover, the use of porous metal material for dental augment 10, 110 promotes ingrowth of bone from mandible M or a maxilla into the body of the augment, thereby establishing a permanent and stable foundation of support to which any number of dental implants can be attached or detached as needed. At the same time, the solid material of the inserts allow for secure fixation of dental implants 50, 50' to the porous metal foundation provided by augment 10, 110, including the potentially ingrown bone facilitated by the porous metal material.

While this invention has been described as having exemplary designs, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) can be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A dental augment system, comprising:
a porous metal augment sized and shaped for implantation into at least one of a mandible and a maxilla, the porous metal augment having an insert bore extending from a superior surface to an inferior surface of the porous metal augment, wherein the inferior surface includes a counterbore surrounding an inferior end of the insert bore;
a solid metal insert having a shoulder at a inferior end, a shaft extending from the shoulder to a superior end, and a threaded bore, the solid metal insert configured to be received and entirely positioned within the insert bore at the inferior surface such that the shaft is received within the insert bore and the shoulder is received within the counterbore such that an inferior surface of the shoulder is one of: flush with the inferior surface of the porous metal augment and recessed within the inferior surface of the porous metal augment; and
a dental implant having a threaded implant portion configured to be received within the superior surface of the porous metal augment and threadably engage the threaded bore of the solid metal insert.

2. The dental augment system of claim 1, wherein the insert bore has a noncircular cross-section perpendicular to a longitudinal axis of the insert bore, and wherein an external surface of the shaft has a noncircular cross-section perpendicular to a longitudinal axis of the solid metal insert.

3. The dental augment system of claim 1, wherein the solid metal insert is coupled to the porous metal augment by at least one of electric resistance welding and diffusion bonding.

4. The dental augment system of claim 1, wherein the insert bore extends from a superior end at the superior surface of the porous metal augment to the inferior end at the inferior surface of the porous metal augment.

5. The dental augment of claim 1, wherein, when the shoulder is flush with the inferior surface of the porous metal augment, a thickness of the shoulder is equal to a depth of the counterbore.

6. The dental augment system of claim 1, wherein, when the shoulder is recessed within the inferior surface of the porous metal augment a thickness of the shoulder is less than a depth of the counterbore.

7. The dental augment system of claim 1, wherein the insert bore has a circular cross-section perpendicular to a longitudinal axis of the insert bore and the counterbore has a noncircular cross-section perpendicular to the longitudinal axis of the insert bore.

8. The dental augment system of claim 7, wherein the shaft has a circular cross-section in a plane perpendicular to a longitudinal axis of the solid metal insert and the shoulder has a noncircular cross-section in a plane perpendicular to the longitudinal axis of the solid metal insert.

9. The dental augment system of claim 1, wherein the solid metal insert includes at least one of titanium and cobalt-chrome-molybdenum, and wherein the porous metal augment includes porous tantalum.

* * * * *